(12) United States Patent
Dillmore et al.

(10) Patent No.: US 8,389,290 B2
(45) Date of Patent: Mar. 5, 2013

(54) BIOSENSOR DEVICE FOR SENSING AMPHIPATHIC ANALYTES

(75) Inventors: W. Shannon Dillmore, Raleigh, NC (US); J. Bruce Pitner, Durham, NC (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 958 days.

(21) Appl. No.: 12/325,880

(22) Filed: Dec. 1, 2008

(65) Prior Publication Data

US 2012/0100631 A1    Apr. 26, 2012

Related U.S. Application Data

(60) Provisional application No. 60/991,534, filed on Nov. 30, 2007.

(51) Int. Cl.
  *G01N 21/76* (2006.01)
  *G01N 33/92* (2006.01)
(52) U.S. Cl. ............ 436/172; 436/71; 424/486
(58) Field of Classification Search .............. None
  See application file for complete search history.

(56) References Cited

U.S. PATENT DOCUMENTS

| | | | | |
|---|---|---|---|---|
| 3,299,176 | A * | 1/1967 | Longworth | 525/192 |
| 4,071,508 | A * | 1/1978 | Steckler | 526/287 |
| 7,063,103 | B2 | 6/2006 | Guler et al. | |
| 7,316,909 | B2 | 1/2008 | Pitner et al. | |
| 7,316,919 | B2 * | 1/2008 | Childs et al. | 435/177 |
| 7,326,538 | B2 | 2/2008 | Pitner et al. | |
| 7,469,392 | B2 | 12/2008 | Mang et al. | |
| 7,951,605 | B2 * | 5/2011 | Pitner et al. | 436/95 |
| 2004/0234962 | A1 | 11/2004 | Alarcon et al. | |
| 2005/0042704 | A1 | 2/2005 | Alarcon et al. | |
| 2005/0239155 | A1 | 10/2005 | Alarcon et al. | |
| 2006/0079808 | A1 | 4/2006 | Allard | |
| 2006/0280652 | A1 | 12/2006 | Pitner et al. | |
| 2008/0305007 | A1 | 12/2008 | Cai et al. | |

FOREIGN PATENT DOCUMENTS

WO    WO 2006/073429    7/2006

OTHER PUBLICATIONS

Richieri, G.V., et al. 1992 The Journal of Biological Chemistry 267(33): 23495-23501.*
Mun, G.A., et al. 2004 Journal of Polymer Science Part B: Polymer Physics 42: 1506-1513.*
GenBank Accession No. NM 013068, accessed date 2000.
Huber et al., "Fatty acid-specific fluorescent probes and their use in resolving mixtures of unbound free fatty acids in equilibrium with albumin", Biochemistry, 45(48):14263-14274 (2006).
Smith et al., "The adipocyte fatty acid-binding protein binds to membranes by electrostatic interactions", J. Biol. Chem., 274(50):35325-35330 (1999).
Richieri et al., "Thermodynamics of fatty acid binding to engineered mutants of the adipocyte and intestinal fatty acid-binding proteins", J. Biol. Chem., 273(13):7397-7405 (1998).

* cited by examiner

*Primary Examiner* — Marsha Tsay
(74) *Attorney, Agent, or Firm* — Morgan, Lewis & Bockius LLP

(57) ABSTRACT

The current invention relates to sensing elements and devices comprising at least one amphipathic lipid-binding protein or fatty acid binding protein, wherein the binding proteins are associated with a luminescent reporter group. The binding proteins and luminescent reporter groups are encapsulated within a hydrogel matrix that comprises at least one co-monomer, wherein the co-monomer is present at a concentration that decreases or inhibits micelle formation of the amphipathic lipid. Binding of the amphipathic lipid or fatty acid to the appropriate binding protein can produce at least one detectable change in the property of the luminescent reporter group.

17 Claims, 12 Drawing Sheets

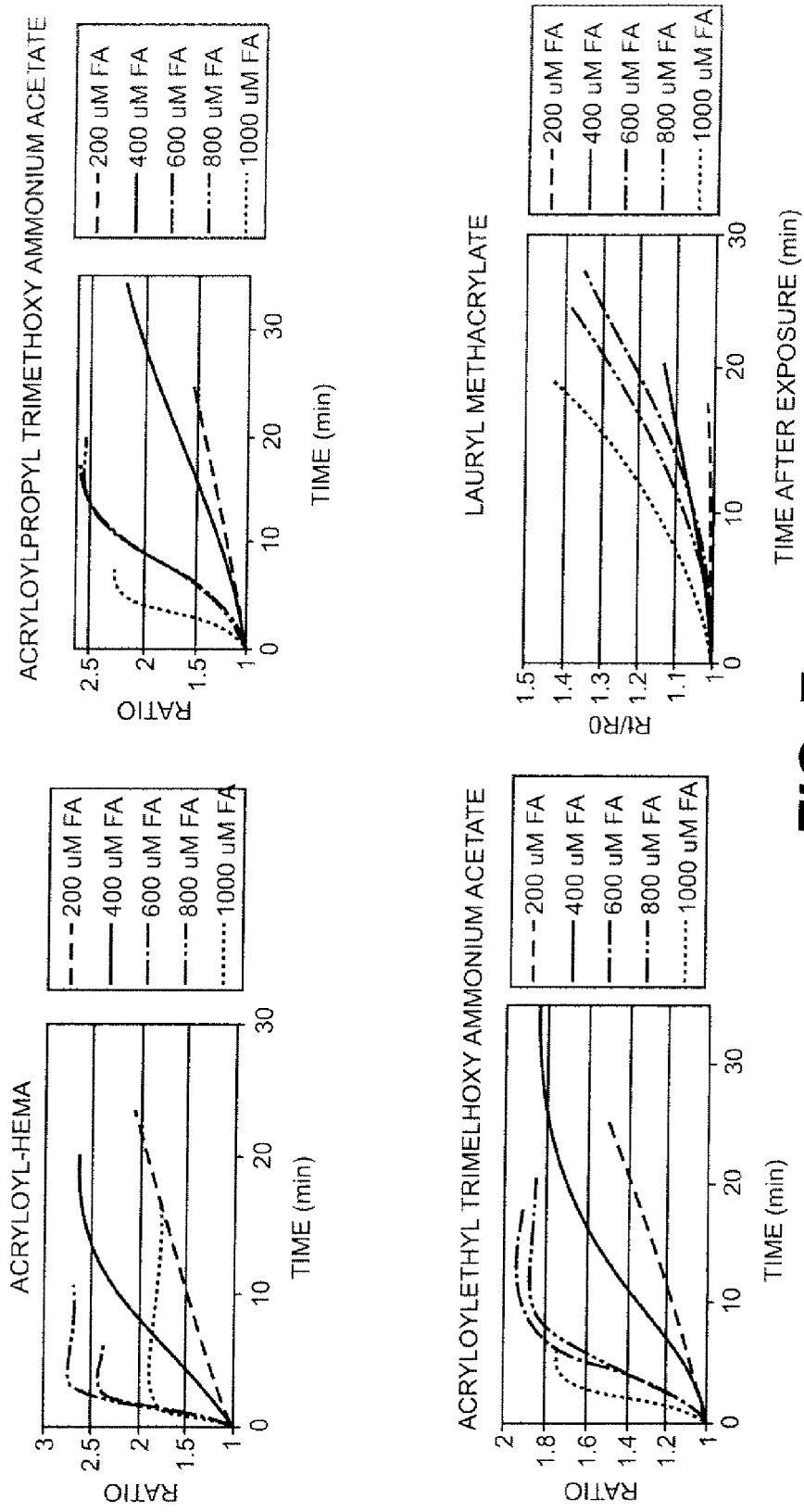
FIG. 7 CON'T

BIOSENSOR DEVICE FOR SENSING AMPHIPATHIC ANALYTES

CROSS-REFERENCE TO RELATED APPLICATIONS

This application claims priority to U.S. Provisional Application 60/991,534, filed 30 Nov. 2007, which is incorporated by reference in its entirety.

STATEMENT REGARDING FEDERALLY SPONSORED RESEARCH OR DEVELOPMENT

Part of the work performed during development of this invention was funded in part by a grant from the U.S. Army Medical Research and Material Command (USAMRMC) under TMM contract number W81XWH-04-1-0815. The U.S. Government may have certain rights in this invention.

BACKGROUND OF THE INVENTION

1. Field of the Invention

The current invention relates to sensing elements and devices comprising at least one amphipathic lipid-binding protein or fatty acid binding protein, wherein the binding proteins are associated with a luminescent reporter group. The binding proteins and luminescent reporter groups are encapsulated within a hydrogel matrix that comprises at least one co-monomer, wherein the co-monomer is present at a concentration that decreases or inhibits micelle formation of the amphipathic lipid. Binding of the amphipathic lipid or fatty acid to the appropriate binding protein can produce at least one detectable change in the property of the luminescent reporter group.

2. Background of the Invention

Recent studies have shown that elevated free fatty acid (FFA) levels have a negative impact on human health. Individuals with FFA levels significantly higher than those of the general population are at increased risk of mortality, heart disease and insulin resistance, a hallmark of type 2 diabetes. Despite these relationships, FFA levels are not monitored by physicians nearly as routinely as other analytes such as cholesterol, triglycerides and glucose. One obstacle to FFA joining this panel of routinely tested species is the method of quantification. The two most commonly used approaches involve either the use of radiolabeled reagents with complex instrumentation, or an enzyme-based colorimetric assay requiring strict time and temperature controls. Neither approach is ideal in a point-of-care setting. Knudsen and co-workers recently described an alternative approach using enzymatic modification and a fluorescently labeled binding protein, but this method still requires complex sample handling and has a slow (>1 hour) turnaround time.

The limitation of acrylodan-labeled fatty acid binding protein is that the CMC (critical micelle concentration) of fatty acids occurs at ~75 µM. At fatty acid concentrations above the CMC, the concentration of free fatty acid remains essentially constant. Because acrylodan-labeled fatty acid binding protein only measures monomeric free fatty acid, the CMC places an upper limit on the measurable fatty acid content in a sample. Higher concentrations can only be quantified following dilution of biological samples. Clearly there exists a need, particularly for in vivo monitoring, for a biosensor that can directly measure fatty acids in samples without the need for dilution.

SUMMARY OF THE INVENTION

The current invention relates to sensing elements and devices comprising at least one amphipathic lipid-binding protein or fatty acid binding protein, wherein the binding proteins are associated with a luminescent reporter group. The binding proteins and luminescent reporter groups are encapsulated within a hydrogel matrix that comprises at least one co-monomer, wherein the co-monomer is present at a concentration that decreases or inhibits micelle formation of the amphipathic lipid. Binding of the amphipathic lipid or fatty acid to the appropriate binding protein can produce at least one detectable change in the property of the luminescent reporter group.

DETAILED DESCRIPTION OF THE INVENTION

Figure 1:
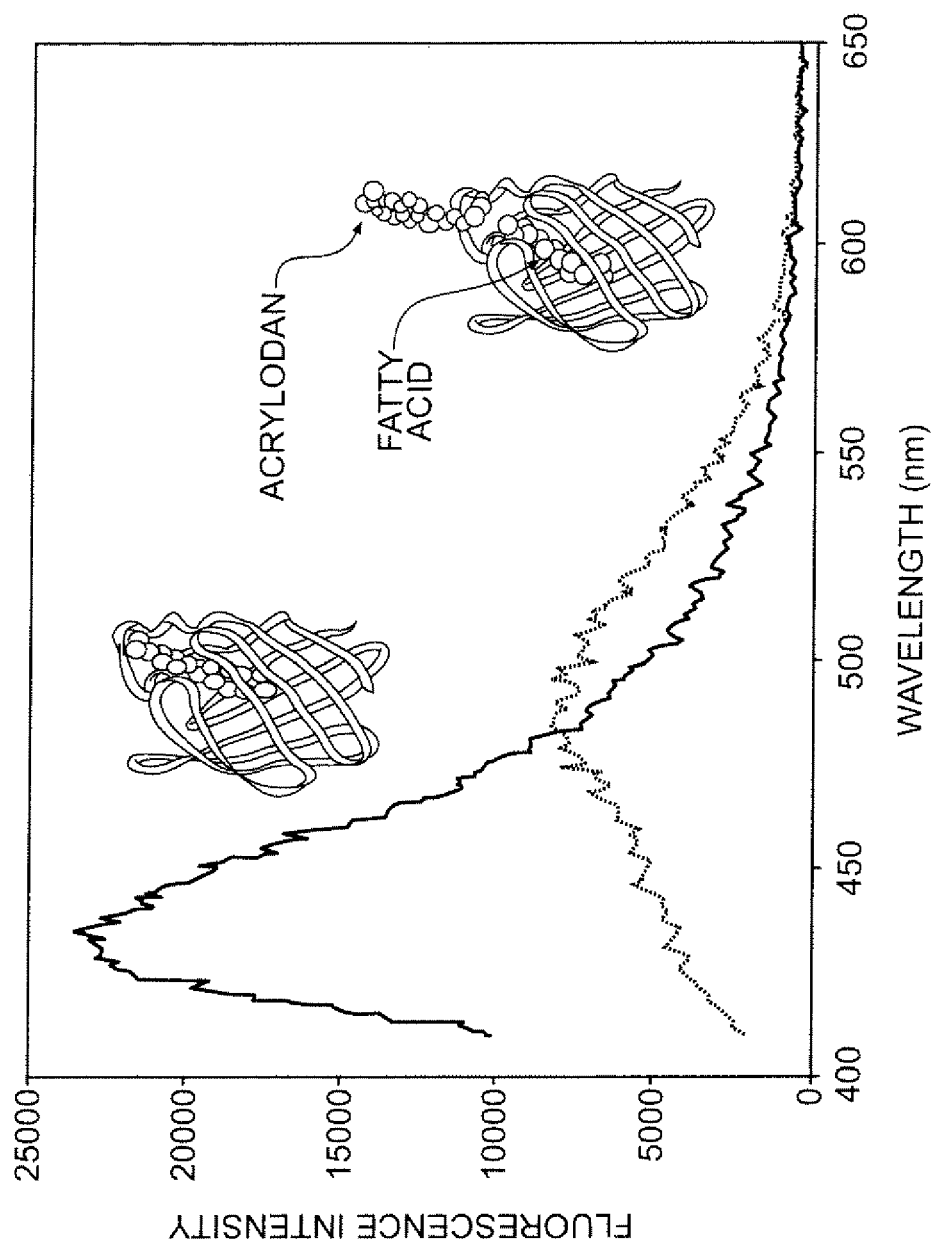
FIG. 1 depicts a simulation of the predicted change in structure and fluorescence spectrum of acrylodan-labeled fatty acid binding protein upon binding of a fatty acid molecule.

The term "amphipathic lipid" refers to any suitable lipid wherein the hydrophobic portion of the lipid material partitions into the hydrophobic phase, while a hydrophilic portion partitions into the aqueous phase. Hydrophilic characteristics derive from the presence of polar or charged groups such as, but not limited to, carbohydrates, phosphato, carboxylic, sulfato, amino, sulfhydryl, nitro, hydroxy and the like. Hydrophobicity can be conferred by the inclusion of apolar groups that include, but are not limited to, long chain saturated and unsaturated aliphatic hydrocarbon groups and such groups substituted by one or more aromatic, cycloaliphatic or heterocyclic group(s). Examples of classes of amphipathic lipids include, but are not limited to, fatty acids, phospholipids, aminolipids, sphingolipids, glycosphingolipids, diacylglycerols and beta-acyloxyacids.

The term "fatty acid" used herein refers to the saturated acids of the acetic acid series, including both normal and branched chain, and also related unsaturated acids, certain substituted acids, and aliphatic acids containing alicyclic substituents. The naturally occurring fatty acids, with a few exceptions, are higher straight chain unsubstituted acids containing an even number of carbon atoms. The fatty acids may be, but are not limited to, saturated fatty acids such as lauric acid, myristic acid, palmitic acid, stearic acid, arachidic acid and lignoceric acid. Alternatively, the fatty acids may also be unsaturated fatty acids, such as, but not limited to, palmitoleic acid, oleic acid, linoleic acid, linolenic acid and arachidonic acid.

The term "micelle" used herein refers to aggregates of amphipathic molecules present in an aqueous solution, wherein the hydrophobic domains of the molecules of the aggregate are oriented toward the interior of the micelle and the hydrophilic domains are in contact with the aqueous solution. Micelle structures include, but are not limited to, spherical, laminar, cylindrical, ellipsoidal, vesicular and lamellar.

The term "critical micelle concentration" of a compound is used herein to mean the maximal concentration at which an amphipathic compound exists as a non-aggregated, single molecule in solution. When the concentration of the compound exceeds its critical micelle concentration, then molecular aggregates, e.g., micelles, are formed. The molecular aggregation that occurs when the critical micelle concentration is reached need not be a micelle, provided that the amphipathic compounds agglomerate.

As used herein, the term "matrix" refers to any three dimensional network of materials, including, but not limited to, synthetic or biological polysaccharide matrices, collagen matrices, hydrogels, polymer networks, soft microfabricated structures, e.g., from polydimethylsiloxane (PDMS), gels of lyotropic liquid crystals, and matrices prepared from bacterial cell secretions. The materials of the matrices may be chemically crosslinked, photochemically crosslinked, or physically crosslinked. The matrix may be any that permits free diffusion of the analyte of interest into and out of the matrix, while excluding interfering immune proteins and proteases and allows the binding protein to retain some degree of conformational and/or orientational mobility. The matrix may consist of multiple layers, with an inner layer serving to retain the binding protein, and one or more outer layers to control the permeability and/or achieve biocompatibility. For example, the matrix may be any one of those described in copending, commonly owned U.S. application Ser. No. 10/428,295, filed May 2, 2003, the entire contents of which are incorporated herein by reference. The immobilization may be accomplished either by covalently linking the binding protein to the matrix or by physically entrapping the binding protein within the matrix. In the instance where the matrix physically entraps the binding protein, the matrix pores are sized to retain the binding protein. In the embodiment where the binding protein is attached to the matrix, the sensing element is attached to the matrix using, for example, covalent or ionic linkage. The matrix can be attached to the distal end of a tip, needle and/or an optical conduit such as a fiber, using, for example, adhesives, dip or spin coating, plasma coating, covalent, ionic, or van der Waals interactions, a mechanical connector or combinations thereof.

The term "hydrogel" is used herein as it is used in the art and, in general, refers to a broad class of polymeric materials which are swollen extensively in water but which do not dissolve in water. Generally, hydrogels are formed by polymerizing a hydrophilic monomer in an aqueous solution under conditions where the polymer becomes crosslinked so that a three-dimensional polymer network sufficient to gel the solution is formed. Hydrogels can have a polymeric matrix of proteins and/or polymers. Hydrogels may contain synthetic polymers such as, but not limited to, polymalic acid, polyamino acids, polyacrylic acids, polyethylene glycol, polyvinylpyrrolidone, polyvinyl alcohols, and hydrophilic polyurethanes. Hydrogels may also comprise materials that include, but are not limited to, albumin, collagen, gelatin, starch, celluloses, dextran, polymalic acid, polyamino acids and their co-polymers or lightly cross-linked forms. Other possible materials are polysaccharides and their derivatives. Yet other possible materials include, but are not limited to, sodium alginate, karaya gum, gelatin, guar gum, agar, algin, carrageenans, pectin, locust bean gums, xanthan, starch-based gums, hydroxyalkyl and ethyl ethers of cellulose, and sodium carboxymethylcellulose.

As used herein, the term "co-monomer" refers to a monomer which is copolymerized with at least one different monomer in a copolymerization reaction, the result of which is a copolymer.

The term "biosensor" generally refers to a device that uses specific biochemical reactions mediated by isolated enzymes, immunosystems, tissues, organelles or whole cells to detect chemical compounds, usually by electrical, thermal or optical signals. As used herein, a "biosensor" refers to a protein capable of binding to an analyte which may be used to detect an analyte or a change in analyte concentration by a detector means as herein described.

The term "derivative" as used herein means a compound or molecule whose core structure is the same as or closely resembles that of a parent compound or molecule, but which has a chemical or physical modification, such as different or additional side groups; the term encompasses copolymers of parent compounds.

The term "binding protein" refers to any protein which interacts with specific analytes in a manner capable of providing or transducing a detectable and/or reversible signal differentiable either from when analyte is not present, analyte is present in varying concentrations over time, or in a concentration-dependent manner, by means of the methods described herein. The transduction event includes continuous, programmed, and episodic means, including one-time or reusable applications. Reversible signal transduction may be instantaneous or may be time-dependent providing a correlation with the presence or concentration of analyte is established. In another embodiment, binding proteins are mutated in such a manner as to effect transduction, for example, mutations that increase or decrease the affinity of binding proteins for specific analytes.

As used herein, the term "conformational change" refers to an alteration of the three dimensional orientation of a compound or molecule. It is intended that the term encompasses the alteration of the three dimensional orientation of a single molecule, or molecular aggregate, such as a protein, e.g., the change in the three dimensional orientation of a fatty acid binding protein upon binding of a fatty acid molecule, or complex of proteins.

As used herein, the term "dynamic range" is intended to connote the range of target analyte concentration in which the detectable spectral change is dependent upon the concentration of the target analyte.

The term "reporter group" refers to any molecule that is used to provide a detectable signal, and which can be associated with a binding protein. The detectable signal may be quantifiable, semi-quantifiable or qualitative in nature.

Reporter groups may provide signals detectable by fluorescence, luminescence or other optical signals or qualities, such as lifetime fluorescence, intensity, radioactivity, calorimetric, X-ray diffraction or absorption, magnetism, enzymatic activity, and the like.

In one embodiment, the reporter group is a fluorophore. As used herein, "fluorophore" is used as it is in the art and refers to a molecule that emits light upon the absorption of energy. Non-limiting examples of fluorophores useful as reporter groups in this invention include acrylodan, fluorescein, coumarins, rhodamines, 5-TMRIA (tetramethylrhodamine-5-iodoacetamide), Quantum Red™ (R-phycoervthrin coupled to (9-(2(or 4)-(N-(2-maleimdylethyl)-sulfonamidyl)-4(or 2)-sulfophenyl)-2,3,6,7,12,13,16,17-octahydro-(1H,5H, 11H,15H-xantheno(2,3,4-ij:5,6,7-i'j')diquinolizin-18-ium salt), Texas Red™ (9-(2(or 4)-(N-(2-maleimdylethyl)-sulfonamidyl)-4(or 2)-sulfophenyl)-2,3,6,7,12,13,16,17-octahydro-(1H,5H,11H,15H-xantheno(2,3,4-ij:5,6,7-i'j') diquinolizin-18-ium salt), Cy™ 3 (2-(5-(1-(6-(N-(2-maleimdylethyl)-amino)-6-oxohexyl)-1,3-dihydro-3,3-dimethyl-5-sulfo-2H-indol-2-ylidene)-1,3-propyldienyl)-1-ethyl-3,3-dimethyl-5-sulfo-3H-indolium salt), N-((2-iodoacetoxy)ethyl)-N-methyl)amino-7-nitrobenzoxadiazole (IANBD), 6-acryloyl-2-dimethylaminonaphthalene (acrylodan), pyrene, Lucifer Yellow (6-amino-2,3-dihydro-2-(2-((iodoacetyl)amino)ethyl)-1,3-dioxo-1H-benz(de)isoquinoline-5,8-disulfonic acid salt), Cy™ 5 p-(5-(1-(6-(N-(2-maleimdylethyl)-amino)-6-oxohexyl)-1,3-dihydro-3,3-dimethyl-5-sulfo-2H-indol-2-ylidene)-1,3-pentadienyl)-1-ethyl-3,3-dimethyl-5-sulfo-3H-indolium salt), Dapoxyl® (2-bromoacetamidoethyl)sulfonamide (4-(5-(4-dimethylaminophenyl)oxazol-2-yl)phenyl-N-(2-bromoacetamidoethyl)sulfonamide), (N-(4,4-difluoro-1,3,5,7-tetramethyl-4-bora-3a,4a-diaza-s-indacene-2-yl)-iodoacetamide (Bodipy507/545 IA), N-(4,4-difluoro-5,7-diphenyl-4-bora-3a,4a-1-diaza-s-indacene-3-propionyl)-N'-iodoacetylethylenediamine (BODIPY®. 530/550 IA), 5-((((2-iodoacetyl) amino)ethyl)amino)naphthalene-1-sulfonic acid (1,5-IAEDANS), carboxy-X-rhodamine, 5/6-iodoacetamide (XRIA 5,6). Other fluorophores that exhibit environmentally-sensitive fluorescence properties include squaraines, coumarins, aza-coumarins, IAZCO, benzodiaxoazoles, and dyes derived from Nile Red such as INR. These fluorophores are described in pending U.S. Pregrant Publication No. 2006/0280652, which is incorporated herein by reference. Additional fluorophores are described in U.S. application Ser. Nos. 12/250,953, filed 14 Oct. 2008 and 12/124,553, filed 21 May 2008, respectively, both of which are incorporated by reference.

The reporter group may be attached to the binding protein by any conventional means known in the art. For example, the reporter group may be attached via amines or carboxyl residues on the protein. In one embodiment, N-hydroxy-succinimide (NHS) esters are used to crosslink the reporter group to primary amino groups on the binding protein. Alternatively, cysteine or other amino acid groups may be engineered into the binding protein to provide sites of attachment for the reporter group. Any thiol-reactive group known in the art may be used for attaching reporter groups such as fluorophores to a native, engineered, or mutated protein's cysteine. For example, acrylates, an iodoacetamide, bromoacetamide, or maleimide are well known thiol-reactive moieties that may be used for this purpose.

A "spectral change" in a fluorophore reporter group may be monitored to detect analyte binding. The "spectral change" that occurs upon analyte binding can be, but is not limited to, a change in fluorescence lifetime, fluorescence intensity, fluorescence polarization, and spectral shifts of fluorescence emission. Such spectral changes may result from changes in the local environment of the fluorophore, such as those resulting from changes in protein conformation. Environmentally-sensitive dyes such as acrylodan and IANBD are particularly useful in this respect. Other spectral changes may result from interactions with the analyte itself or from interactions with a second reporter group, for example when FRET (fluorescence resonance energy transfer) is used to monitor changes in distance between two fluorophores.

The term "detector" as used herein refers to any component, portion thereof, or system of components that can detect the detectable signal generated by the reporter group. In one specific embodiment, the detector can detect at least one property of light including, but not limited to, a charged coupled device (CCD), back-side thin-cooled CCD, front-side illuminated CCD, a CCD array, a photodiode, a photodiode array, a photo-multiplier tube (PMT), a PMT array, complimentary metal-oxide semiconductor (CMOS) sensors, CMOS arrays, a charge-injection device (CID), CID arrays, etc. The detector can be adapted to relay information to a data collection device for storage, correlation, and/or manipulation of data, for example, a computer, or other signal processing system.

Amphipathic lipid-binding proteins possess ideal qualities for use in the present invention. Examples of amphipathic lipid-binding proteins include, but are not limited to fatty acid binding proteins (FABPs). The FABPs are a family of proteins that are expressed at least in the liver, intestine, kidney, lungs, heart, skeletal muscle, adipose tissue, abnormal skin, adipose, endothelial cells, mammary gland, brain, stomach, tongue, placenta, testis, retina. The family of FABPs is, generally speaking a family of small intracellular proteins (~14 kDa) that hind fatty acids and other hydrophobic ligands, through non-covalent interactions. See Smith, E. R. and Storch, J., *J. Biol. Chem.*, 274 (50):35325-35330 (1999), which is hereby incorporated by reference in its entirety. Members of the FABP family of proteins include, but are not limited to, proteins encoded by the genes FABP1, FABP2, FABP3, FABP4, FABP5, FABP6, FABP7, FABP(9) and MP2. Proteins belonging to the FABP include I-FABP, L-FABP, H-FABP, A-FABP, KLBP, mal-1, E-FABP, PA-FABP, C-FABP, S-FABP, LE-LBP, DA11, LP2, Melanogenic Inhibitor, to name a few. In one embodiment, the FABP used in the present invention is a rat fatty-acid binding protein a human adipocyte fatty acid-binding protein and/or a human heart fatty acid-binding protein. The nucleotide sequence of the rat intestinal fatty-acid binding protein (rFABP) is located at GenBank Accession No. NM 013068, the entire record of which is incorporated by reference. The amino acid sequence of the rat intestinal fatty-acid binding protein (rFABP) is located at GenBank Accession No. NM 013068, the entire record of which is incorporated by reference. Additional embodiments include the use of fatty acid binding proteins such as those disclosed in Huber. A. H., et al., *Biochemistry* 45: 14263-14274 (2006), which is incorporated by reference. The fatty acid binding proteins in Huber et al. have been mutated to alter their specificity toward individual fatty acids, which can, in turn, resolve the identity of constituents of mixtures of free fatty acids.

In one embodiment, the amphipathic lipid-binding protein may be synthesized as a recombinant protein from the gene encoding the amphipathic lipid-binding protein of interest using standard recombinant protein techniques such as those disclosed in Sambrook, J. and Russell, D., Molecular Cloning: A Laboratory Manual, 3$^{rd}$ Ed., Cold Spring Harbor Laboratory Press, Cold Spring Harbor, N.Y. (2001), which is incorporated by reference in its entirety.

Figure 2A:
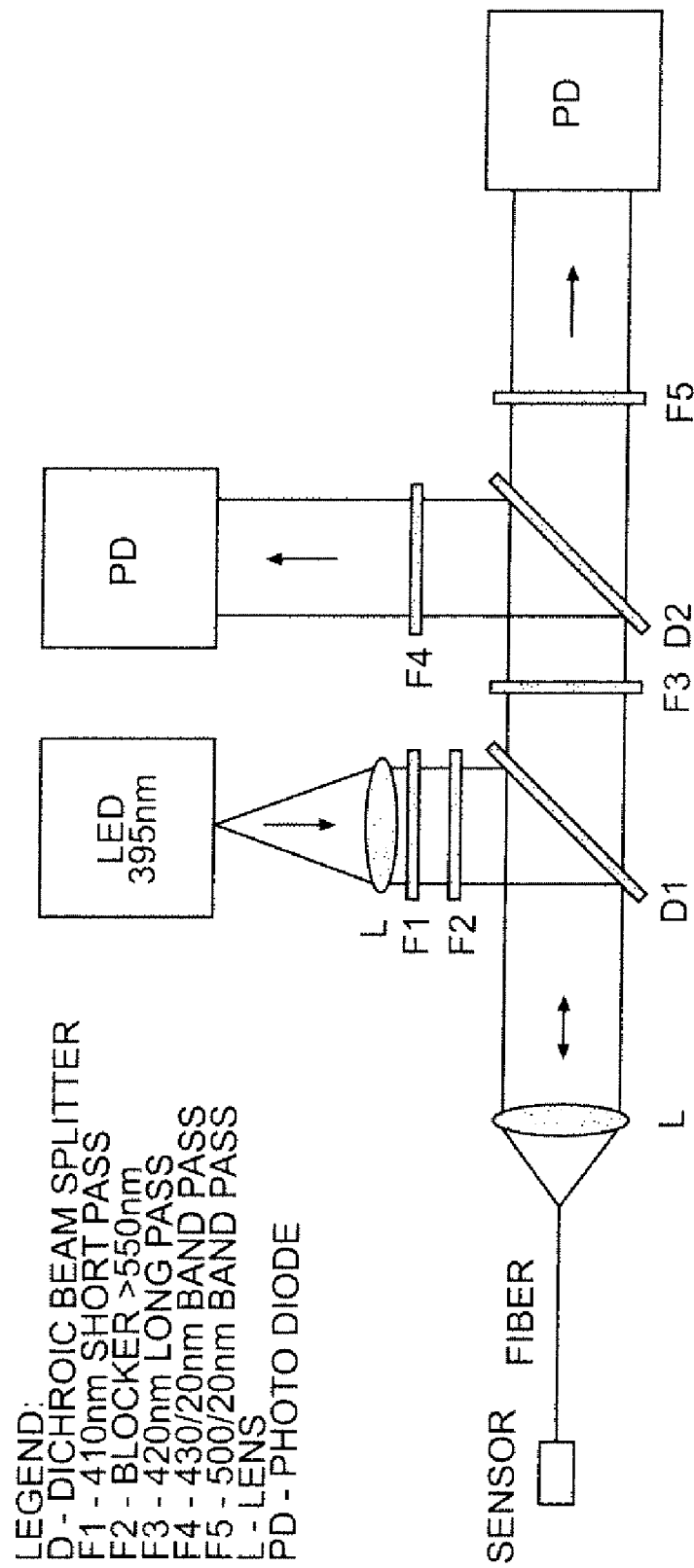
FIG. 2A depicts the optical system used in the biosensor.

In one embodiment, the amphipathic lipid-binding protein can be labeled with acrylodan to generate acrylodan-labeled amphipathic lipid-binding protein. Techniques for labeling proteins with acrylodan are well known in the art. For example, techniques are well known for covalently attaching acrylodan to lysine, which could be used to attach acrylodan to lysine 27 of the rFABP used in select embodiments of the present invention. The labeled amphipathic lipid-binding protein generates a spectral change upon binding of the amphipathic lipid-binding protein to its binding target, e.g., free fatty acids. The spectral change induced upon target molecule binding may be due to, but is not limited to, an alteration in the local environment of the label bound to the amphipathic lipid binding protein. Spectral changes can then be measured by any suitable detection method known in the art to determine the extent of target molecule binding. In one particular embodiment, the detection device comprises a photo diode and a dichroic beam splitter as shown in FIG. 2A. It is envisioned that this method may be easily adapted for use with virtually any amphipathic lipid-binding proteins to detect the binding or absence of binding of appropriate amphipathic lipids.

In one embodiment of the current invention, the amphipathic lipid-binding protein is present within a hydrogel, comprising at least one backbone molecule, which is the chemical unit that forms the bulk of the hydrogel. The backbone molecule may be, but is not limited to, a chemical molecule comprised of a polymer of ethylene glycol units (PEG) and one or more different chemical moieties that may serve a number of purposes. The ethylene glycol units may be arranged in a linear or branched conformation, or a combination of the two; the length of the molecule may comprise as few as 1-2 ethylene glycol units and as many as thousands or more. Alternatively, hydrogels may contain, for example, polysaccharides such as agarose, dextran, carrageenan, alginic acid, starch, cellulose, or derivatives of these such as, e.g., carboxymethyl derivatives, or a water-swellable organic polymer such as, e.g., polyvinyl alcohol, polyacrylic acid, polyacrylamide, polyethylene glycol, copolymers of styrene and maleic anhydride, copolymers of vinyl ether and maleic anhydride and derivates thereof. Appended chemical moieties may be necessary to facilitate cross-linking of the backbone molecule into the larger polymeric hydrogel. In one embodiment, a methacrylate chemical group is suitable for cross-linking into a hydrogel through a free radical polymerization process. Other functional groups may be appended to the backbone molecule to serve as chemical tethers for attachment of the amphipathic lipid-binding protein. These functional groups may be chosen from, but are not limited to, acrylate, methacrylate, maleimide, N-hydroxysuccinimide, amine, thiol, alkyne, azide, aldehyde, epoxide, quinone and cyclopentadiene. In yet another embodiment, the backbone molecule may be either poly(ethylene glycol)dimethacrylate (PEGDMA) or acryloyl-polyethylene glycol-N-hydroxy succinimide (acryloyl-PEG-NHS), the structures of which are shown below. The examples are not intended to be limiting as many common chemical variants of these compounds well known in the art may also be used.

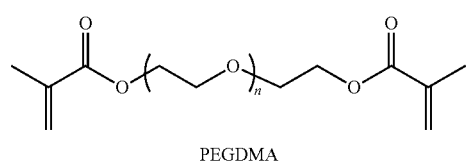

PEGDMA

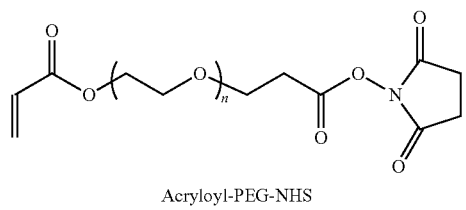

Acryloyl-PEG-NHS

In one embodiment of the current invention, a co-monomer is included in the hydrogel. The co-monomer can be used, among other things, to disrupt micelle formation of amphipathic lipids within the hydrogel. These co-monomers, if used to disrupt micelle formation, comprise a chemical moiety that inhibits or decreases micelle formation within the hydrogel and a functional group that facilitates cross-linking into the hydrogel. The functional group that facilitates cross-linking and the moiety that inhibits or decreases micelle formation may or may not be the same. The latter functional group may be, but is not limited to, a methacrylate, acrylate or olefin group. These co-monomers, by way of disrupting micelle formation, extend the dynamic range in which free fatty acid concentrations can be accurately determined. In one embodiment, the dynamic range may extend from about 0.01 mM to about 1.5 mM. In another embodiment, the dynamic range may extend from about 0.05 mM to about 1.0 mM. In another embodiment, the dynamic range may extend from about 0.02 mM to about 0.8 mM. Of course, the extension of the dynamic range is not limited to those ranges enumerated above. In addition to micelle disruption, in some embodiments, the co-monomer also modifies the ionic and/or hydrophobic properties of the hydrogel to tailor the diffusion of specific analytes into and out of the hydrogel. The diffusion of the analyte may be, but need not be limited to, increasing or decreasing the rate of diffusion of ionic and/or hydrophobic analytes into and out of the hydrogel.

In yet another embodiment, the co-monomer bears a net positive or negative charge. This charge can arise from a variety of functional groups including, but not limited to, amines (primary, secondary, tertiary or quaternary), phosphates, sulfates, carboxylates, imidazoles, and guanidines. The co-monomer confers this positive or negative charge on the hydrogel upon cross-linking. A selection of charged co-monomers is shown below. These examples are not intended to be limiting as many common chemical variants of these compounds well known in the art may also be used.

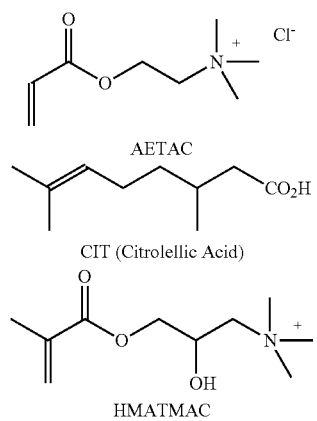

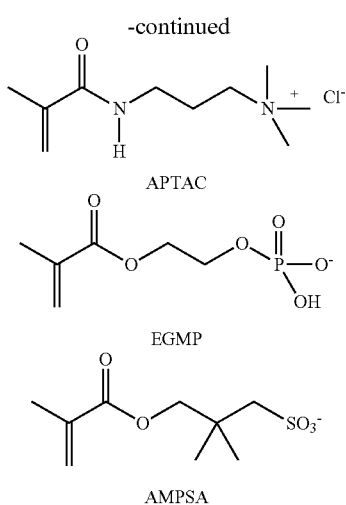

APTAC

EGMP

AMPSA

In a further embodiment, the hydrogel is lipophilic wherein the major component of the co-monomer is a chemical moiety with a lipophilic and/or hydrophobic character. This property can arise from a variety of functional groups including, but not limited to, linear, branched or cyclic chains of methylene groups (examples of these include hexyl, cyclohexyl, octyl, isobutyl, and dodecyl groups), unsaturated alkyl groups and aromatic groups. The co-monomer confers this lipophilic/hydrophobic property on the hydrogel upon cross-linking. A selection of lipophilic/hydrophobic co-monomers is shown below. These examples are not intended to be limiting as many common chemical variants of these compounds well known in the art may be also be used.

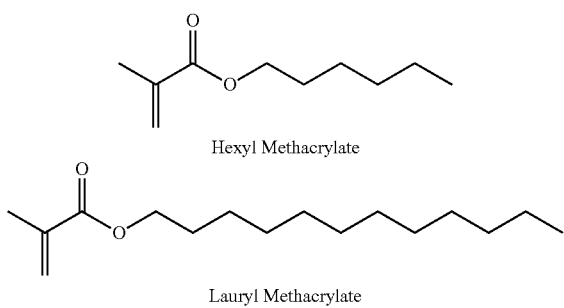

Hexyl Methacrylate

Lauryl Methacrylate

One embodiment of the present invention provides a biosensor which may be used for analyte sensing in vitro or in vivo. The binding protein within a polymeric matrix that may or may not include a co-monomer, comprises the biosensor which, in certain embodiments, may be further be constrained within a needle or tip, or similar object, providing it remains permeable to the analyte. In one embodiment, the needle or tip may be designed to pierce the skin to allow the sensing element to contact body fluids. When used in an in vivo application, the binding protein will be exposed to a physiological range of analyte concentrations, and determination of a change in analyte concentration could include, but not be limited to, continuous, programmed, and episodic detection means. The labeled binding protein provides a detectable and reversible signal change when exposed to varying analyte concentrations, and the detectable and reversible signal can be related to the concentration of the analyte. The polymeric matrix-encapsulated binding protein biosensors may have a dynamic range from micromolar to molar analyte concentrations without requiring reagent consumption. In some embodiments, their sensitivity to an analyte may enable the biosensors to be used to measure the low analyte concentrations known to be present in low volume samples of interstitial fluid. The biosensors may, in other embodiments, be implanted into or below the skin of a mammal's epidermal-dermal junction to interact with the interstitial fluid, tissue, or other biological fluids. The binding protein biosensors of the present invention provide a means to monitor analyte continuously, episodically, or "on-demand" as would be appropriate to the user or to the treatment of a condition. In yet another embodiment, the hydrogel matrix produces minimal or no detectable adverse reactions with the body. Adverse reactions for implants may include, but are not limited to, inflammation, protein fouling, tissue necrosis, immune response and leaching of toxic materials.

In one embodiment, the biosensor, comprising one or more binding proteins and co-monomers encapsulated within a polymeric matrix or hydrogel, may be immobilized at the end of the optical fiber or inside a disposable tip that interfaces with an optical fiber. Immobilization of the sensing element on the optical fiber or inside the disposable tip may be accomplished by depositing a thin layer of the biosensor, for example, by dip or spin coating, covalent attachment, plasma treatment, and the like directly onto the optical fiber or tip. In another embodiment, the sensing element can be first immobilized in a polymer matrix and the matrix then attached to the optical conduit, or tip either by adhesives, injection molding, dip or spin coating, plasma coating, vacuum deposition, ink jet technology, covalent, ionic, or van der Waals interactions, by mechanical attachment, or any combination thereof. It will be obvious to the skilled artisan that the proximal and distal ends of the optical fiber may be either end of the optical fiber, until the biosensor is oriented for use.

In yet another embodiment, the optical system is capable of determining the spectral change of the reporter group by passing light from an electromagnetic excitation source down the optical conduit to the distal end containing the sensing element. The optical system may also monitor and interpret the return signals generated by the reporter group. The spectral change of the reporter group, either wavelength, intensity, lifetime, energy transfer efficiency, or polarization, change in response to analyte binding or unbinding from the binding protein, may be measured using any convenient detection method well known in the art.

EXAMPLES

Example 1

Figure 2B:
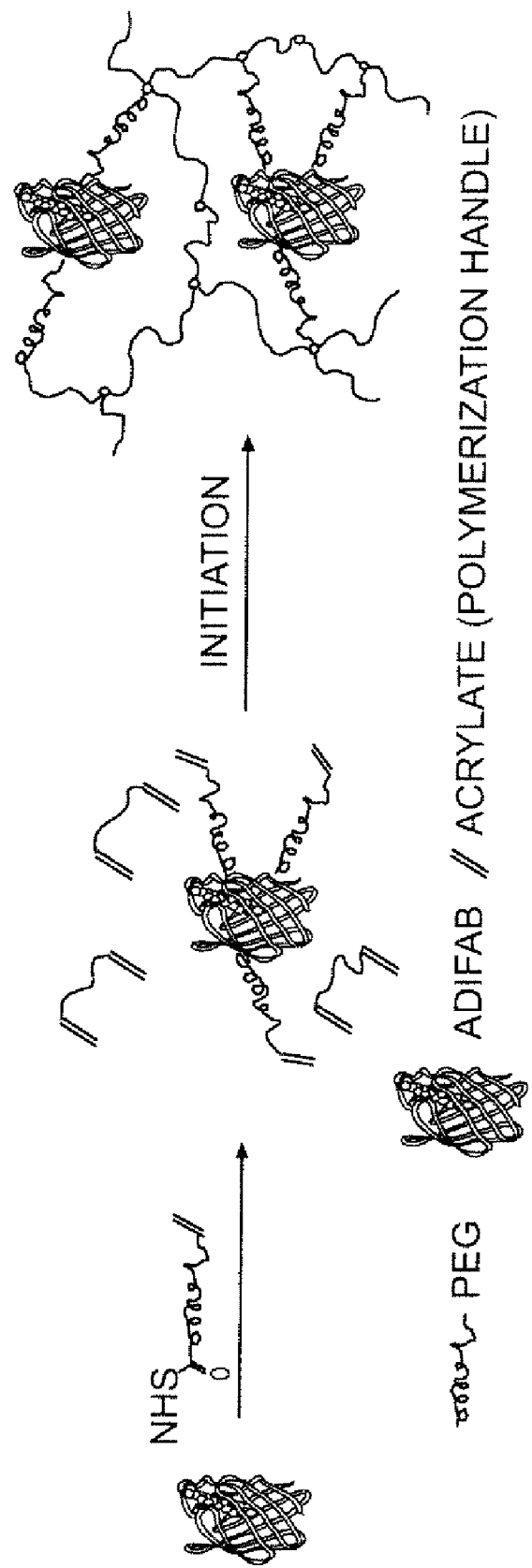
FIG. 2B depicts a method utilized to cross-link acrylodan-labeled fatty acid binding protein within a hydrogel matrix

Acrylodan-labeled fatty acid binding protein was crosslinked to the PEG-based hydrogel backbone molecule as depicted in FIG. 2B. A 1 mg aliquot of lyophilized acrylodan-labeled fatty acid binding protein was dissolved in 550 µL of 1×PBS buffer (pH 7.4) to produce a 120 µM solution. A 60 mM solution of acryloyl-PEG-NHS (APS; MW-3400 Da) was produced in 0.1 M MES buffer (pH 6.3). The protein and PEG solution were mixed at a 5:1 protein:PEG ratio, and allowed to react at room temperature for 2 hours. The reaction mixture was then incubated at 4° C. overnight. PEGylated acrylodan-labeled fatty acid binding protein was purified from un-reacted PEG reagent by using a NAP-10 column (Amersham Biosciences, Piscataway, N.J.). PEGylation of acrylodan-labeled fatty acid binding protein was demonstrated by standard PAGE electrophoresis on a BioRad 4-15% acrylamide gradient gel (120V, 45 min). The gel was stained using a SilverQuest silver staining kit from Invitrogen (Madison, Wis.).

Example 2

Sensor Fabrication. Fiber optic-needle sensors were assembled by depositing a small drop of non-fluorescing glue roughly 20 mm from the tip of an optical fiber, then sliding the fiber through the shaft of an 18-gauge needle until the fiber optic tip was located in the center of the needle bevel. The glue was allowed to cure for 15 minutes before additional glue was added to secure the base of the needle to the optical fiber. Stability of the sensor was assessed by vigorous shaking. The sensors were then taped or otherwise affixed to a solid support such as cardboard. 500 μL microcentrifuge tubes were attached to the solid support such that the tips of the needles rested against the bottom of the tubes. After mixing, prepolymer solution was added to the tubes (typically 40 μL each) and allowed to cure for 30-60 minutes. To form the hydrogel matrix, the prepolymer formulation was optimized for maximum stability and fluorescence. After mixing the solution, adding APS last, 40 μL of the resulting solution was deposited into each tube and allowed to cure around the needle tip for 30-60 minutes. The needle/gel complex was then removed from the tube, and excess gel was removed from the needle tip. Previous observations demonstrated that acrylodan-labeled fatty acid binding protein can bind to a contaminant if the protein is allowed to directly contact plastic surfaces. To remove any contaminants, sensors were exposed to 500 μM arachidonate (to flush contaminant from the binding pocket) for one hour then rinsed in at least 10 mL PBS buffer for four hours to remove the arachidonate. Sensors were then ready for use in binding experiments.

Example 3

In one embodiment, the basic formulation of the polymeric matrix in the absence of co-monomer was as follows. 39.6 μL of PBS buffer was mixed with 42 μL of a 60% PEGDMA (w/v) solution and 1.2 μL of a 25% (v/v) TEMED solution. 36 μL PEGylated acrylodan-labeled fatty acid binding protein was then added to the mixture and the solution was vortexed briefly. After adding 1.2 μL 10% (w/v) APS, the solution was again vortexed briefly. Polymeric matrix compositions containing a co-monomer component contained 25 mol % co-monomer with respect to PEG content. All formulations were mixed as described above. Individual formulations are given below with each separate co-monomer used. When the co-monomer is 2-hydroxy-3-methacryloxypropyl trimethyl ammonium chloride (HMATMAC): 38.7 μL PBS buffer, 42 μL 60% PEGDMA (w/v) in water, 36 μL PEGylated acrylodan-labeled fatty acid binding protein (~100 μM), 1.2 μL APS (10% w/v), 1.2 μL TEMED (v/v), 0.9 μL HMATMAC (note: this formulation contained only 15 mol % co-monomer). When the co-monomer is ethylene glycol methacrylate phosphate (EGMP): 39.6 μL PBS buffer, 39.74 μL 60% PEGDMA (w/v) in water, 36 μL PEGylated acrylodan-labeled fatty acid binding protein (~100 μM), 1.2 μL APS (10% w/v), 1.2 μL TEMED (v/v), 1.26 μL EGMP. When the co-monomer is 2-acrylamido-2-methyl-1-propane sulfonic acid (AMPSA): 39.6 μL PBS buffer, 39.5 μL 60% PEGDMA (w/v) in water, 36 μL PEGylated acrylodan-labeled fatty acid binding protein (~100 μM), 1.2 μL APS (10% w/v), 1.2 μL TEMED (v/v), 1.16 μL AMPSA. When the co-monomer is [2-(Acryloxy)ethyl]-trimethylammonium chloride (AETAC): 39.9 μL PBS buffer, 38.8 μL 60% PEGDMA (w/v) in water, 36 μL PEGylated acrylodan-labeled fatty acid binding protein (~100 μM), 1.8 μL APS (10% w/v), 1.8 μL TEMED (v/v), 1.7 μL AETAC (80% in water). When the co-monomer is [2-(Methacryloylamino)propyl]-trimethylammonium chloride (APTAC): 37.7 μL PBS buffer, 39.2 μL 60% PEGDMA (w/v) in water, 36 μL PEGylated acrylodan-labeled fatty acid binding protein (~100 μM), 1.8 μL APS (10% w/v), 1.8 μL TEMED (v/v), 3.5 μL APTAC (50% in water). When the co-monomer is Citronellic acid: 28.4 μL PBS buffer, 39.7 μL 60% PEGDMA (w/v) in water, 12 μL DMSO, 36 μl PEGylated acrylodan-labeled fatty acid binding protein (~100 μM), 1.24 APS (10% w/v), 1.2 μL TEMED (v/v), 1.55 μL citronellic acid. When the co-monomer is Hexyl methacrylate: 28.3 μL PBS buffer, 39.7 μL 60% PEGDMA (w/v) in water, 12 μL DMSO, 36 μL PEGylated acrylodan-labeled fatty acid binding protein (~100 μM), 1.2 μL APS (10% w/v), 1.2 μL TEMED (v/v), 1.66 μL hexyl methacrylate. When the co-monomer is lauryl methacrylate: 28.6 μL PBS buffer, 38.7 μL 60% PEGDMA (w/v) in water, 12 μL DMSO, 36 μL PEGylated acrylodan-labeled fatty acid binding protein (~100 μM), 1.2 μL APS (10% w/v), 1.2 μL TEMED (v/v), 2.26 μL lauryl methacrylate Example 4

For the measurement of the biosensor fluorescence an optical device was constructed which was capable of exciting in the ultra-violet spectral region and detecting two different wavelength regions simultaneously. A schematic of the optics is given in FIG. 2A. A light emitting device (LED) was chosen with a central emission wavelength at 395 nm. To reduce noise and the influence of ambient light, a lock-in technique was applied. A 410 nm short pass in front of the LED was used to cut off any broad luminescence background from the LED, which could potentially overlap with the fluorescence coming from the biosensor. The collimated LED light was diverted by a dichroic beam-splitter and focused on the fiber core of the biosensor. The emission light coming from the fiber passed the first dichroic mirror and a 420 mm long pass filter. After that the light was spectrally separated by a second dichroic beam-splitter, which is highly reflective below 455 nm. The blue spectral component passed a 430/20 nm band pass filter and the green spectral component passed a 500/20 nm filter before impinging on the photodiode. Interrogation of FFA-containing solutions was performed by simply immersing the tip of the fiber in the sample for a determined period of time, then returning the sensor to buffer. Fluorescence readings were typically taken every three seconds for the duration of the experiment.

Example 5

Figure 3:
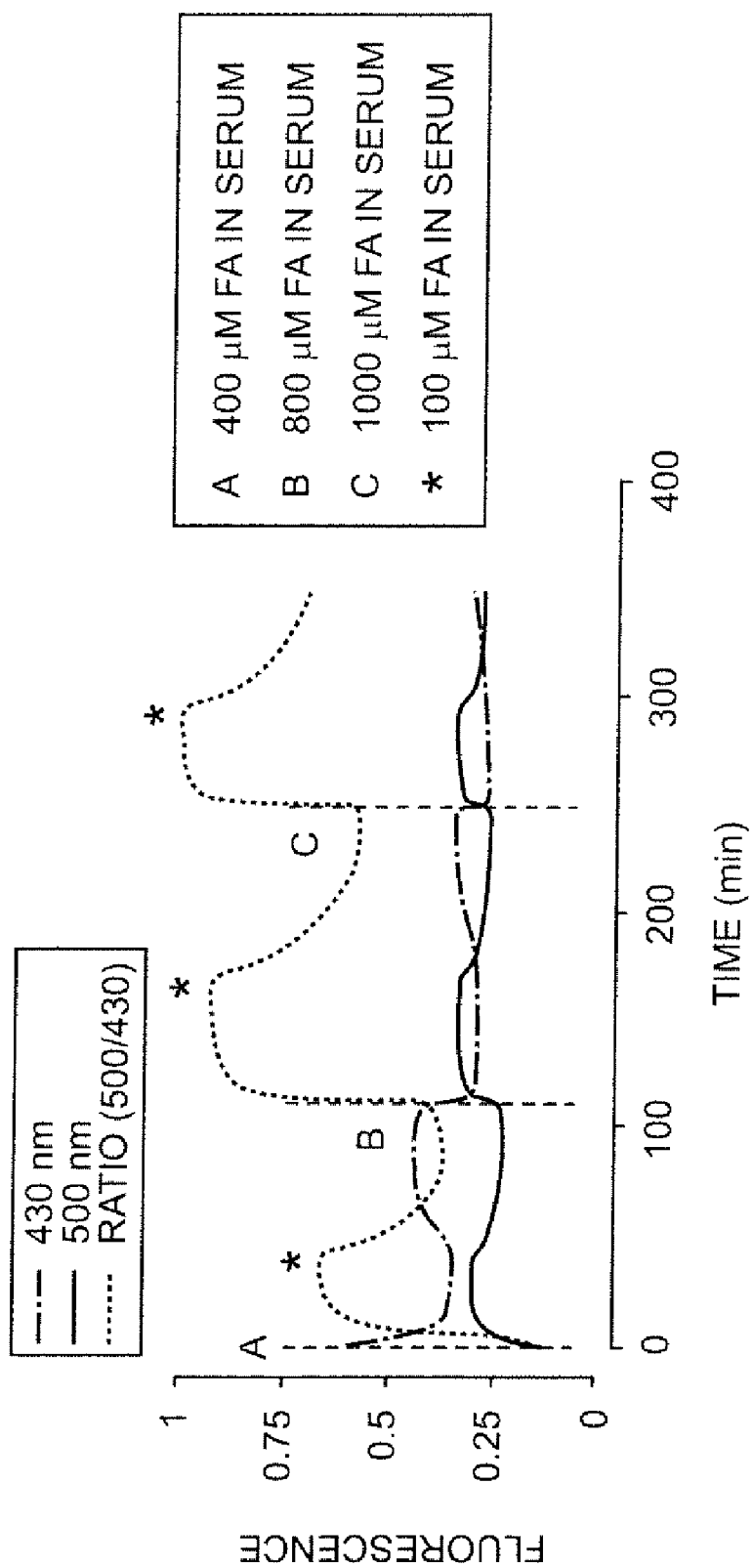
FIG. 3 depicts a real-time sensor response to fatty acid interrogation (corrected for drift due to photobleaching) wherein the hydrogel does not contain a co-monomer.
Figure 4:
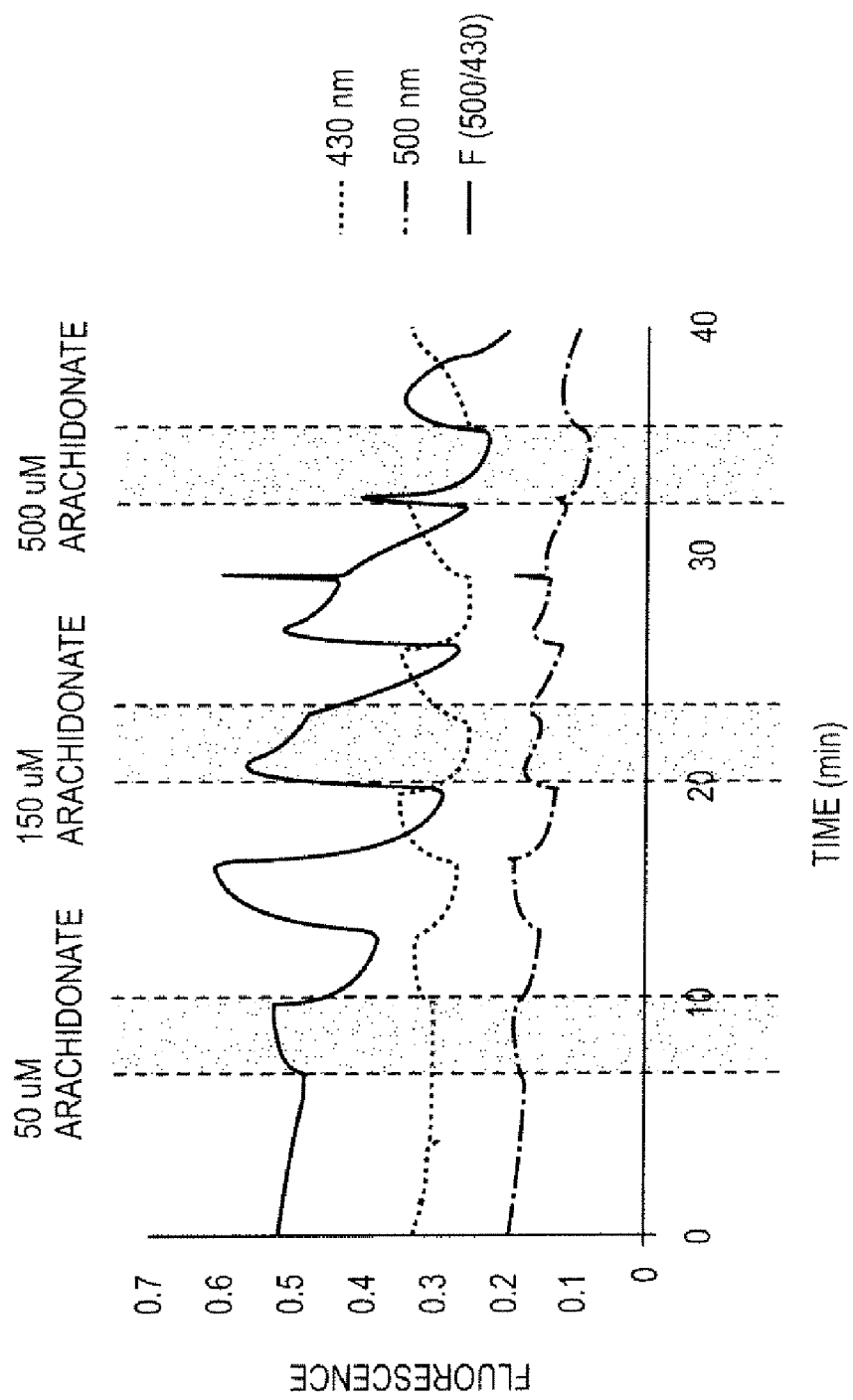
FIG. 4 depicts a demonstration of the signal-inhibiting effect of micelle formation. An initial rise in fluorescence ratio (500/430 nm) was observed after initial exposure of the sensor to arachidonate. At higher concentrations of arachidonate, however, the ratio rapidly decreased after the initial rise. After a return to buffer, the ratio increased as the micelle complex dissociated.

An embodiment of the fatty acid sensor comprises a hydrogel containing no co-monomer. A real-time biosensor response to fatty acid interrogation (corrected for drift due to photobleaching) in the absence of co-monomer is depicted in FIG. 3. The biosensor was tested in a continuous format by exposing the biosensor to a range of arachidonate-containing solutions, ranging from 25-125 μM arachidonate, for three minutes, then returned to buffer until the signal was completely reversed. After complete signal reversal, the sensor was again exposed to arachidonate. At higher arachidonate concentrations, however, an inversion of the ratio during fatty acid exposure was observed (FIG. 4). This inversion may be attributed to the "micelle effect." Monomeric fatty acids are known to aggregate into micelles upon reaching their critical micelle concentration. Micelles may also incorporate other amphiphilic molecules such as dyes into these structures. Upon micelle formation, the absorbance spectrum of the dye shifts towards the red end of the spectrum. In the case of the sensor, this would result in a drop in fluorescence due to decreased absorption at 390 nm. One compelling piece of evidence for this hypothesis is that the ratio inversion is identically matched by the signal at 500 nm. The source of signal at 500 nm is fluorescence from acrylodan exposed to solvent that is exposed to the micellar environment. The ratio inversion has no signature at 430 nm. The source of signal for the 430 nm signal is fluorescence from acrylodan within the binding pocket, where no dye-micelle interaction is possible. The critical micelle concentration (cmc) of arachidonate has been reported at 76 µM, which is within a factor of two of where the micelle effect is observed for the sensor described herein. The elevated cmc in this sensor case may be due to a slow rate of diffusion of the fatty acid into the hydrophilic gel matrix or by the environment in the hydrogel rendering micelle formation slightly less energetically favorable than in solution.

Example 6

Figure 5:
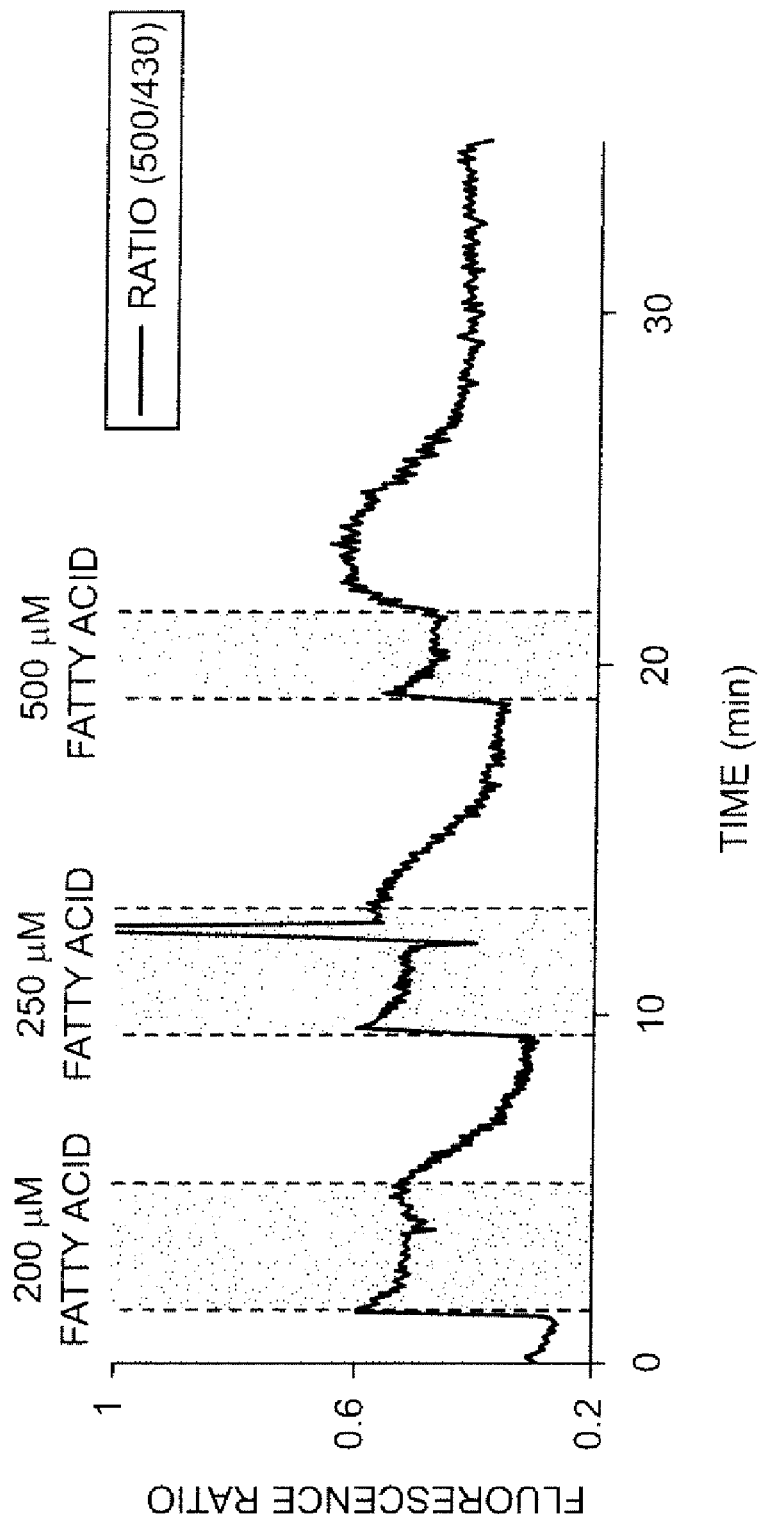
FIG. 5 depicts a demonstration of the micelle inhibiting effect of addition of an ionic co-monomer (AETAC) to the biosensor matrix. The inversion of signal and drop in ratio was less pronounced than that observed with no co-monomer.

Incorporation of a co-monomer into the hydrogel matrix. The micelle effect places an upper limit on the fatty acid concentrations that can be measured in solution. To increase this upper limit, a range of co-monomers were incorporated into the gel to make micelle formation less favorable. Because the manipulation of critical micelle levels is not trivial, a wide variety of co-monomers were tested: positively charged co-monomers that may interact electrostatically with the fatty acids, and negatively charged and/or lipophilic co-monomers that may interact with the monomeric fatty acids and increase the entropic penalty of micelle formation. Nearly all co-monomers tested (incorporated in the gel at 25 mol %) had an effect on the sensor response to fatty acid levels. An illustrative example is given below with AETAC, an ionic co-monomer (FIG. 5). In contrast to FIG. 3, where no co-monomer was present, the micelle effect is nearly eliminated for 200 and 250 µM arachidonate, and the complete reversal of signal seen in the co-monomer-less gel was ameliorated with the AETAC co-monomer.

Example 7

Figure 6:
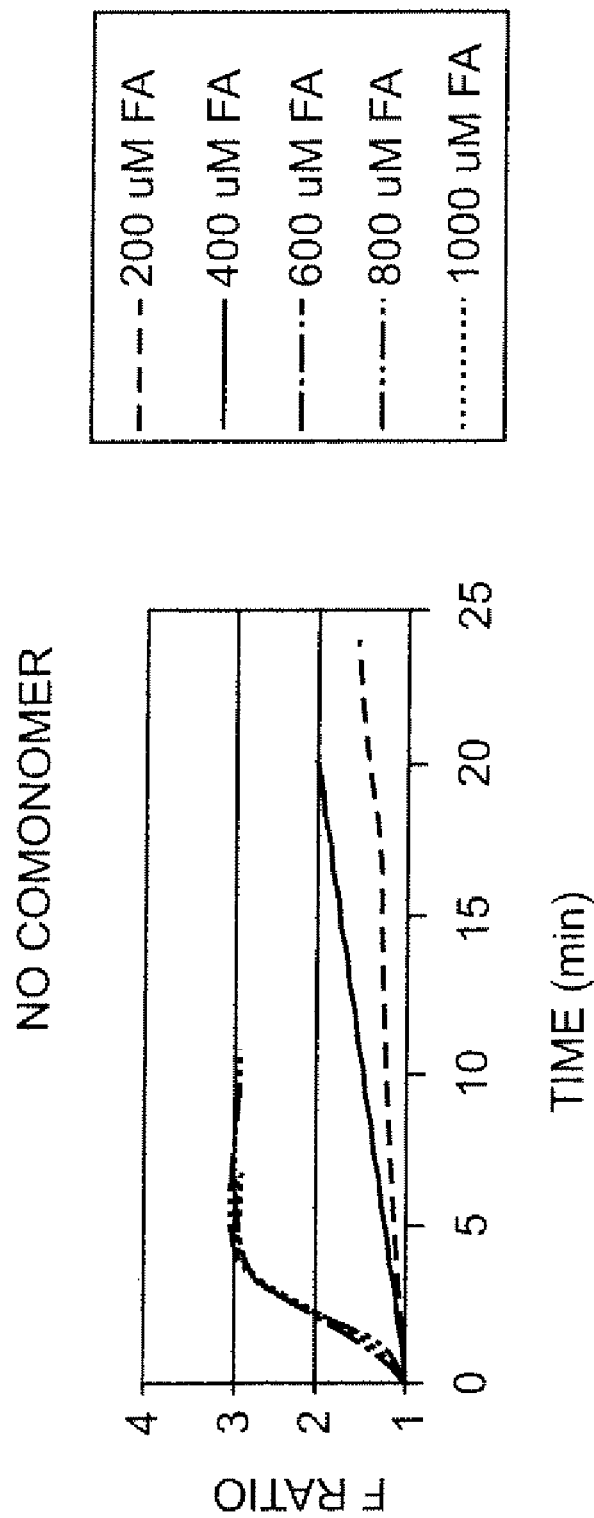
FIG. 6 depicts biosensor performance in episodic mode in the absence of co-monomer. The signals generated at 600, 800 and 1000 µM FA were virtually identical.

Fatty acid sensing in an episodic format. An episodic sensor, i.e, a sensor one in which a single reading is taken, of the fatty acid sensor of Example 6 may also be useful in a clinical setting as a routine measure of fatty acid levels. In this format, the biosensor was exposed to a sample for about 20 minutes and the change in fluorescence ratio was monitored. After exposure, the sensor was returned to buffer until the ratio returned to the starting level, or until an unchanging ratio was reached. Five fatty acid concentrations (200, 400, 600, 800 and 1000 µM) within the physiologically relevant range were chosen. The magnitude of the change should have been proportional to the level of free fatty acid in the sample. A graph of a biosensor in the absence of co-monomer is given in FIG. 6. The micelle effect was observed at about 4 minutes, and the sensor did not distinguish between samples with free fatty acid levels at or above 600 µM.

Example 8

Figure 7:
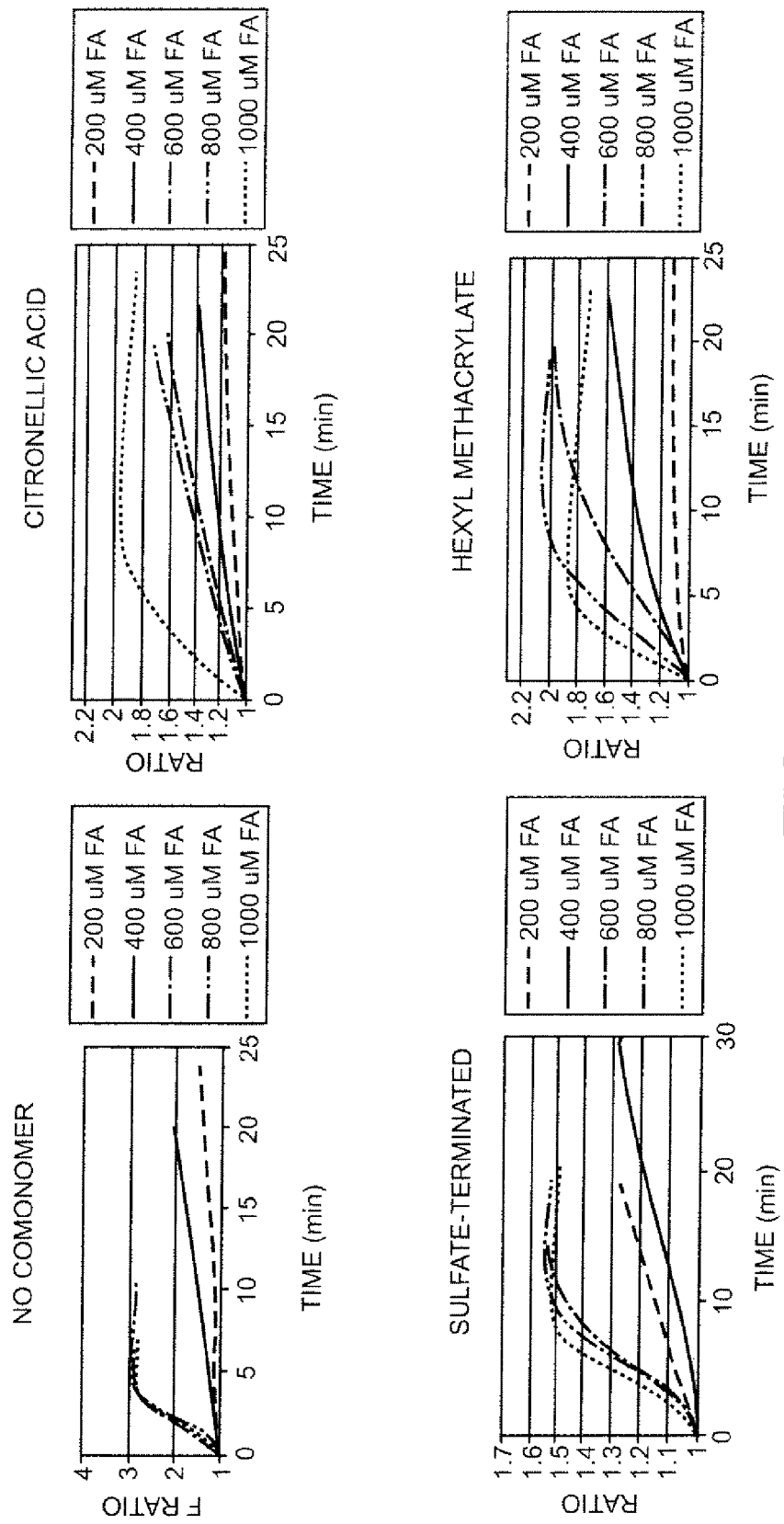
FIG. 7 depicts a change in fluorescence ratio versus time for five different fatty acid concentrations using sensing elements constructed from co-monomers as described in the examples. All have an effect on biosensor response to fatty acid levels as compared to sensing elements without co-monomer.

Effect of hydrogel co-monomer on sensing range in epi-sodic format. Seven co-monomers, incorporated at 25 mol % compared to PEGDMA, were incorporated in the sensing matrix. The data are shown in FIG. 7 plus a comparison to the co-monomer-less sensing matrix. Virtually every co-monomer had an effect on sensor response. The lipophilic co-monomers hexyl methacrylate and lauryl methacrylate produced the best separation between all five fatty acid levels measured, and therefore may be the most promising for application in fatty acid sensing.

Example 9

Figure 8:
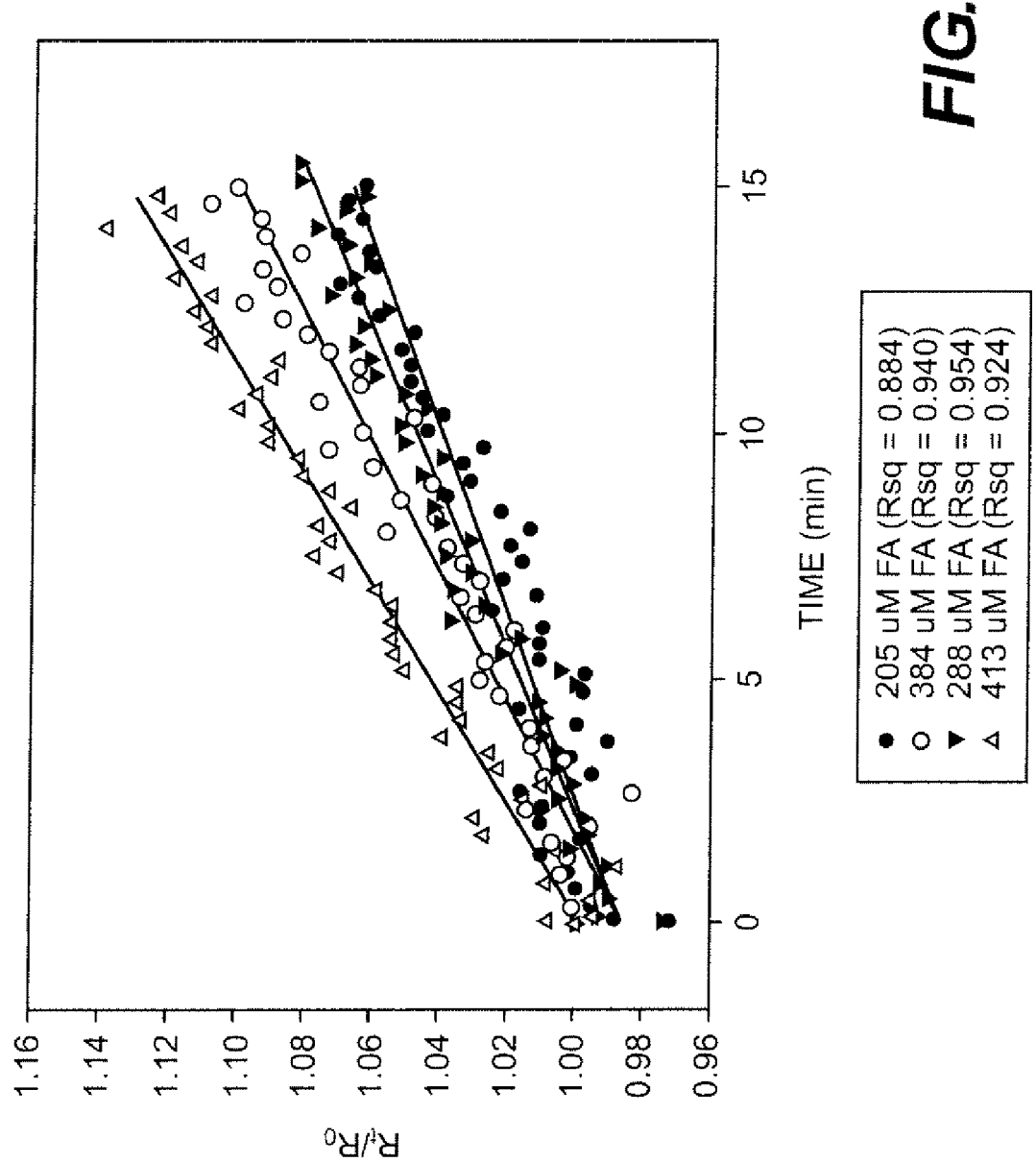
FIG. 8 depicts the change in fluorescence ratio versus time for four human serum samples having different FA concentrations.
Figure 9:
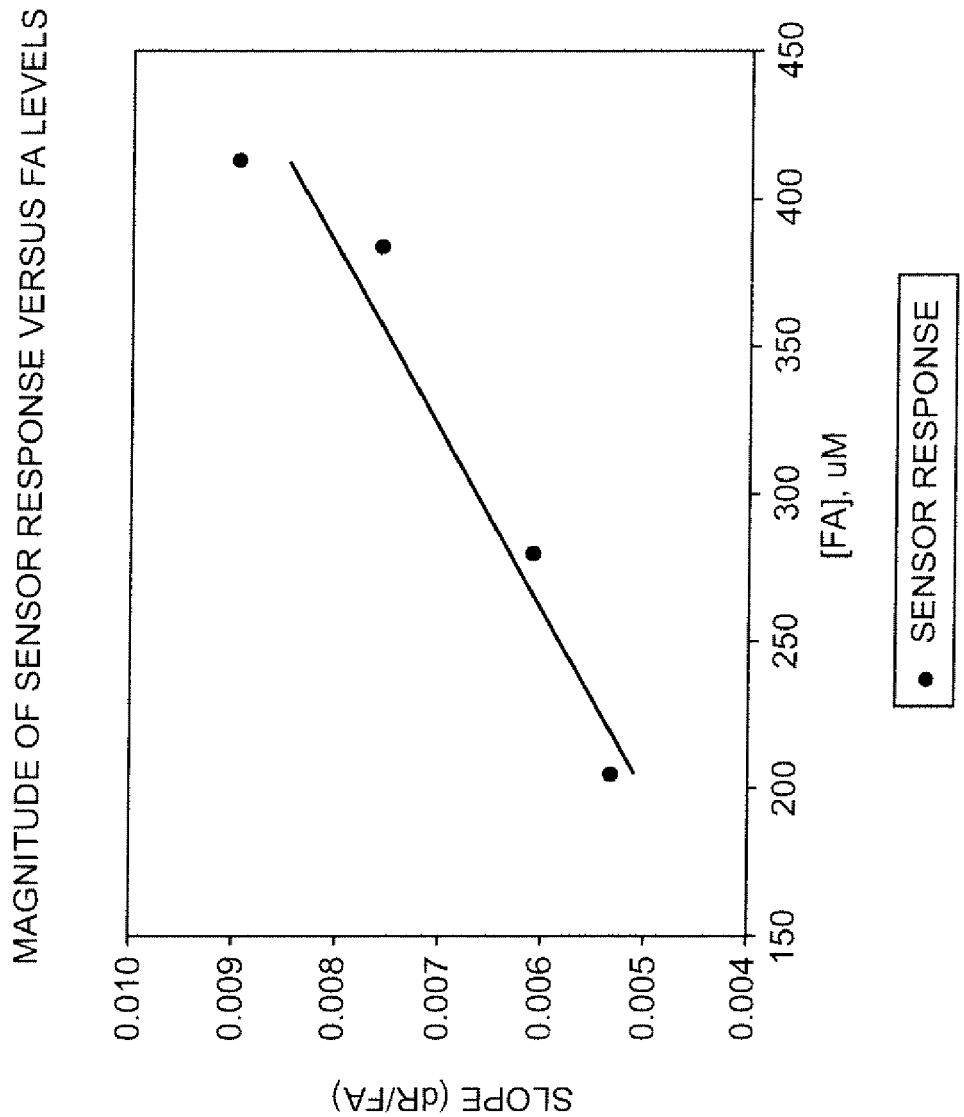
FIG. 9 depicts the slope of sensor response versus free fatty acid concentration in serum.

Sensing fatty acids in biological fluids. As a measure of usefulness in a clinical setting, a sensor with hexyl methacrylate as a co-monomer was fabricated and tested against five human serum samples. An enzymatic-based Wako NEFA kit was used to quantify the true fatty acid content of each serum sample. The raw data from the sensor is shown in FIG. 8. When the data was analyzed using linear regression, a plot of the slope versus FA levels showed good correlation (FIG. 9).

Example 10

Figure 10:
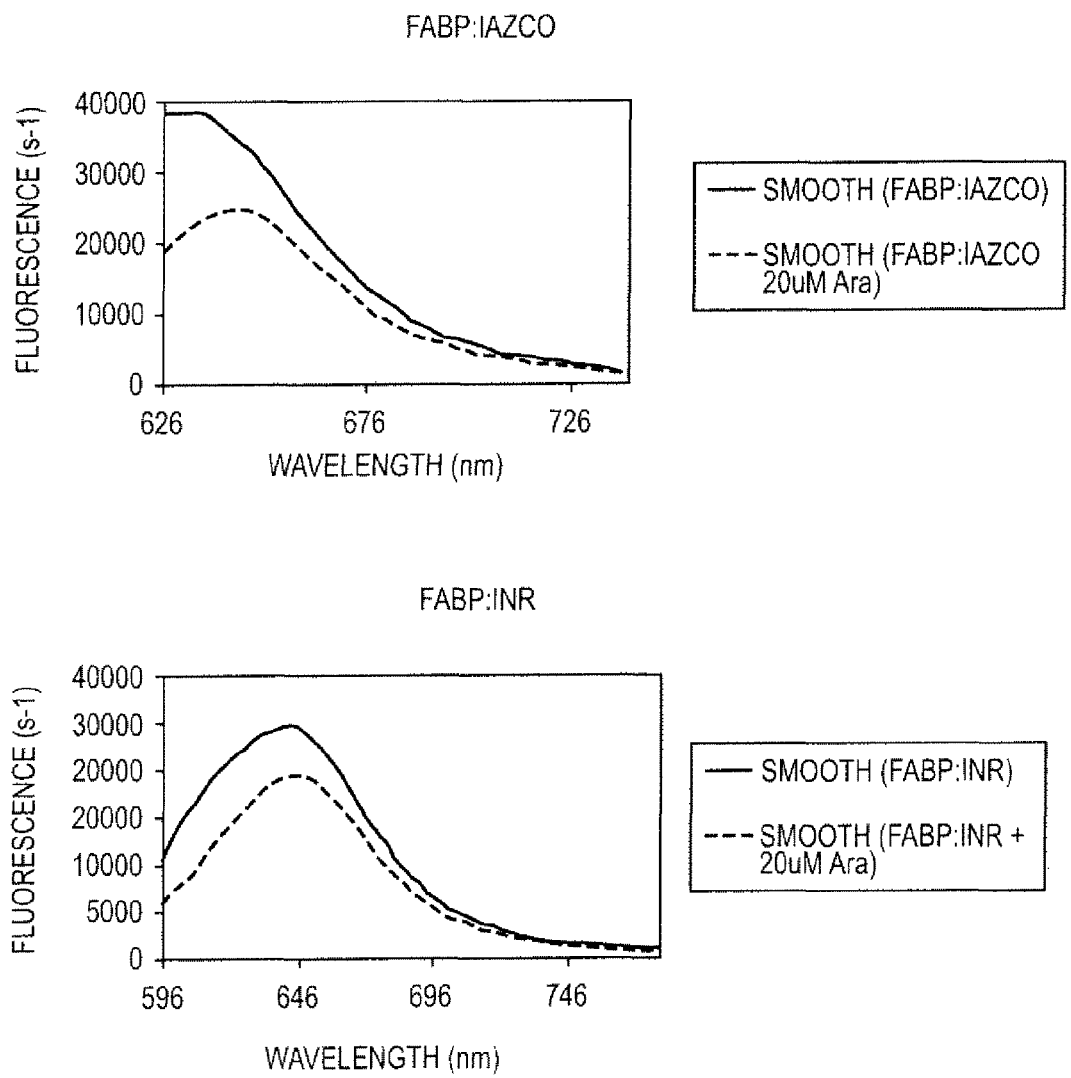
FIG. 10 depicts the response of alternative FABP-dye conjugates to the fatty acid arachidonate in buffer.

Sensing fatty acids with alternative FABP constructs. FABP was synthesized according to previous protocols, such as disclosed in Richieri, G. V., et al. J. Biol. Chem. 267: 23495-501 (1992), which is incorporated by reference. After purification, the protein was labeled with either INR or IAZCO dyes as described in pending U.S. Pregrant Publication No. 2006/0280652. This novel protein-dye conjugate was interrogated with free fatty acid in buffered solution. FIG. 10 shows results of FABP labeled with INR and IAZCO. In both cases, addition of arachidonate lead to both a reduction of intensity and red shift of fluorescence intensity. This example demonstrates that FABP-dye conjugates other than acrylodan-labeled fatty acid binding protein may be used in the modified matrix for fatty acid sensing.

What is claimed is:

1. A sensing element for detecting amphipathic lipids, the sensing element comprising:
   (a) an amphipathic lipid-binding protein and a luminescent reporter group associated therewith, and
   (b) a hydrogel matrix that encapsulates the amphipathic lipid-binding protein and the luminescent reporter group, wherein the hydrogel matrix comprises at least one co-monomer that is, citronellic acid;
   wherein the citronellic acid is present at a concentration that inhibits or decreases micelle formation of the amphipathic lipid, and wherein the binding of the amphipathic lipid to the amphipathic lipid-binding protein results in a detectable change of at least one optical property of the luminescent reporter group.

2. The sensing element of claim 1, wherein the amphipathic lipid binding protein is selected from the group consisting of intestinal fatty acid binding protein, adipocyte fatty acid binding protein and heart fatty acid binding protein.

3. The sensing element of claim 2, wherein the amphipathic lipid binding protein is a rat intestinal fatty acid binding protein.

4. The sensing element of claim 3, wherein said luminescent reporter group is covalently attached to said rat intestinal fatty acid binding protein.

5. The sensing element of claim 4, wherein said luminescent reporter group is a fluorophore.

6. The sensing element of claim 5, wherein said fluorophore is selected from the group consisting of squaraine, benzodiaxoazole, coumarin, aza coumarin, acrylodan, IAZCO, and INR.

7. The sensing element of claim 5, wherein the optical property of the fluorophore is selected form the group consisting of intensity, lifetime, wavelength, polarization, anisotropy and resonance energy transfer efficiency of the fluorescence signal.

8. The sensing element of claim 1, wherein said hydrogel matrix further comprises polyethylene glycol dimethacrylate and polyethylene diacrylate, or the cross-linked product thereof.

9. The sensing element of claim 1, wherein said hydrogel matrix further comprises acryloyl-polyethylene glycol-N-hydroxy succinimide, or the cross-linked product thereof.

10. The sensing element of claim 9, wherein the amphipathic lipid binding protein is selected from the group consisting of intestinal fatty acid binding protein, adipocyte fatty acid binding protein and heart fatty acid binding protein.

11. The sensing element of claim 10, wherein the amphipathic lipid binding protein is a rat intestinal fatty acid binding protein.

12. The sensing element of claim 11, wherein said luminescent reporter group is covalently attached to said rat intestinal fatty acid binding protein.

13. The sensing element of claim 12, wherein said luminescent reporter group is a fluorophore.

14. The sensing element of claim 13, wherein said fluorophore is selected from the group consisting of squaraine, benzodiaxoazole, coumarin, aza coumarin, acrylodan, IAZCO, and INR.

15. The sensing element of claim 13, wherein the optical property of the fluorophore is selected form the group consisting of intensity, lifetime, wavelength, polarization, anisotropy and resonance energy transfer efficiency of the fluorescence signal.

16. The sensing element of claim 9, wherein said hydrogel matrix further comprises polyethylene glycol dimethacrylate and polyethylene diacrylate, or the cross-linked product thereof.

17. The sensing element of claim 1, wherein the detected amphipathic lipids are monomeric free forms of the amphipathic lipids.

* * * * *